(12) United States Patent
Mundey

(10) Patent No.: US 8,337,203 B1
(45) Date of Patent: Dec. 25, 2012

(54) FLEXIBLE DENTAL TOOL APPARATUS AND ASSOCIATED METHOD

(76) Inventor: Shakeya Nina Mundey, Washington, DC (US)

(*) Notice: Subject to any disclaimer, the term of this patent is extended or adjusted under 35 U.S.C. 154(b) by 0 days.

(21) Appl. No.: 12/938,710

(22) Filed: Nov. 3, 2010

(51) Int. Cl.
*A61G 15/16* (2006.01)
*A61C 17/06* (2006.01)

(52) U.S. Cl. ............................................. 433/77; 433/91

(58) Field of Classification Search .................. 433/32, 433/36, 49, 50, 53, 54, 78, 79, 91–96, 77; 604/32, 36, 95.03, 524, 526, 527, 530; 138/121–122, 138/124, 137–138
See application file for complete search history.

(56) References Cited

U.S. PATENT DOCUMENTS

| 5,281,136 A | 1/1994 | Giannella |
| 5,490,716 A | 2/1996 | Naughton |
| 5,520,222 A * | 5/1996 | Chikama ........................ 138/118 |
| 6,315,715 B1 * | 11/2001 | Taylor et al. ................... 600/140 |
| 7,217,241 B2 | 5/2007 | Guenier |
| 2003/0203336 A1 * | 10/2003 | Somodi ........................... 433/91 |

* cited by examiner

*Primary Examiner* — Cris L Rodriguez
*Assistant Examiner* — Matthew Seward

(57) ABSTRACT

A mobile suction unit preferably includes a portable body, a deformably non-resilient appendage connected to the body, and a dental instrument connected to the deformably non-resilient appendage. The deformably non-resilient appendage may be selectively bent from a non-tensioned shape to a curvilinear tensioned shape in such a manner that the deformably non-resilient appendage indefinitely retains the curvilinear tensioned shape while the dental instrument is adapted to be positioned within the patient oral cavity.

9 Claims, 3 Drawing Sheets

FLEXIBLE DENTAL TOOL APPARATUS AND ASSOCIATED METHOD

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to dental tools and, more particularly, to a flexible dental tool apparatus and associated method for providing a user with a means to effectively hold dental tools during a dental procedure.

2. Prior Art

Regular tooth cleaning by a dental hygienist is recommended to remove tartar, mineralized plaque that may develop even with careful brushing and flossing, especially in areas that are difficult for a patient to reach on his own at home. Professional cleaning includes tooth scaling and tooth polishing and debridement if too much tartar has accumulated. This involves the use of various instruments or devices to loosen and remove deposits from the teeth. Two types of dental units used in dentistry are the mobile and the chair mounted types. The chair mounted units are the most common in use.

A typical unit provides the basic utilities for dental treatment including water, compressed air, electricity, and vacuum. It may also include hand piece controls, foot controls, a bracket tray, a tubing flush system, three-way syringes, a cuspidor, and a suction apparatus. The unit should be designed so that it is compact and does not occupy space needed by the assistant. Hose attached equipment, such as hand pieces, syringes and oral evacuation devices, should be conveniently positioned to both the provided and the assistant. However, the latter can pose challenges for the dentist, the assistant, and the patient. These suctioning devices are typically constructed of draping, limp hoses, which can become difficult to manage during a procedure. Moreover, the hose typically has to be held by the patient's hand or mouth, proving quite burdensome and painful.

Accordingly, a need remains for an apparatus in order to overcome the above-noted shortcomings. The present invention satisfies such a need by providing a flexible dental tool apparatus that is convenient and easy to use, is lightweight yet durable in design and designed for providing a user with a means to effectively hold dental tools during a dental procedure.

BRIEF SUMMARY OF THE INVENTION

In view of the foregoing background, it is therefore an object of the present invention to provide a mobile suction unit for extracting fluid and debris from an oral cavity of a patient. These and other objects, features, and advantages of the invention are provided by a mobile suction unit preferably including a portable body, a deformably non-resilient appendage connected to the body, and a dental instrument connected to the deformably non-resilient appendage.

Notably, the deformably non-resilient appendage may be selectively bent from a non-tensioned shape to a curvilinear tensioned shape in such a manner that the deformably non-resilient appendage indefinitely retains the curvilinear tensioned shape while the dental instrument is adapted to be positioned within the patient oral cavity.

In a preferred embodiment, the deformably non-resilient appendage may have a corrugated and non-planar outermost surface.

In an exemplary embodiment, the deformably non-resilient appendage preferably remains connected to the body and the dental instrument while disposed at the curvilinear tensioned shape.

In an exemplary embodiment, the deformably non-resilient appendage may include an internal conduit having a proximal end in fluid communication with the body and further may have a distal end in fluid communication with the dental instrument. Such an internal conduit advantageously remains capable of transferring fluid and debris therein while the deformably non-resilient appendage is disposed at the curvilinear tensioned shape.

In an exemplary embodiment, the deformably non-resilient appendage may include a first deformable sheath directly engaged about an outer surface of the internal conduit. Such a first deformable sheath preferably extends along an entire longitudinal length of the internal conduit. Notably, the first deformable sheath preferably includes a plurality of first spaced grooves formed therein and concentrically disposed about the internal conduit.

In an exemplary embodiment, the deformably non-resilient appendage may further include a second deformable sheath directly engaged about an outer surface of the first deformable sheath. Such a deformable sheath preferably extends along an entire longitudinal length of the first deformable sheath. Notably, the second deformable sheath may include a plurality of second spaced grooves formed therein and concentrically disposed about the internal conduit.

In an exemplary embodiment, the first and second spaced grooves may be concentrically juxtaposed along a longitudinal length of the internal conduit. Each of the second spaced grooves may have a width defined along the longitudinal length of the appendage. In this manner, selected portions of the width are respectively increased and decreased as the second sheath is bent to the curvilinear tensioned shape.

In an exemplary embodiment, the second deformable sheath may further include a plurality tongues statically interfitted within the first spaced grooves respectively. Such tongues preferably exert a shear force directed away from a fulcrum axis about which the appendage is bent such that the first deformable sheath is restricted from returning to the non-tensioned shape.

In an exemplary embodiment, the first deformable sheath preferably remains intercalated between the second deformable sheath and the outer surface of the internal conduit.

In an exemplary embodiment, a holster may be located along a top edge of the body wherein the dental instruments may be removably nested at the holster during non-use.

A method of utilizing a mobile suction unit for extracting fluid and debris from an oral cavity of a patient, the method including the chronological steps of: providing a portable body; providing and connecting a deformably non-resilient appendage to the body wherein the deformably non-resilient appendage may have a corrugated and non-planar outermost surface; and providing and connecting a dental instrument to the deformably non-resilient appendage.

Such a method may further include the chronological steps of: selectively bending the deformably non-resilient appendage from a non-tensioned shape to a curvilinear tensioned shape; positioning the dental instrument within the patient oral cavity; and the deformably non-resilient appendage indefinitely retaining the curvilinear tensioned shape while the dental instrument is positioned within the patient oral cavity.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
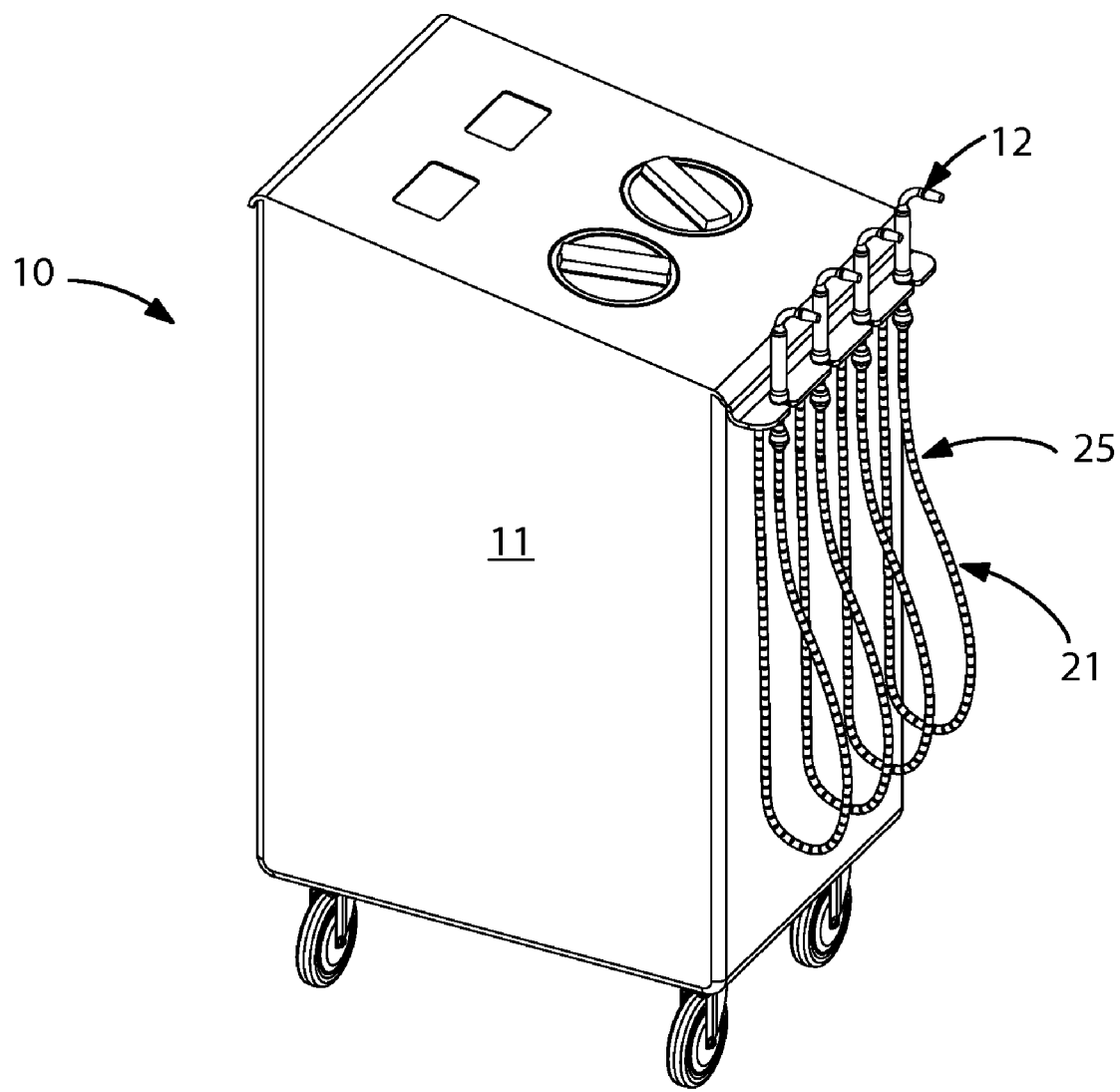
FIG. 1 is a perspective view showing a mobile suction unit for extracting fluid and debris from an oral cavity of a patient, in accordance with the present invention.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "present invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The below disclosed subject matter is to be considered illustrative, and not restrictive, and the appended claims are intended to cover all such modifications, enhancements, and other embodiments which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

Figure 2:
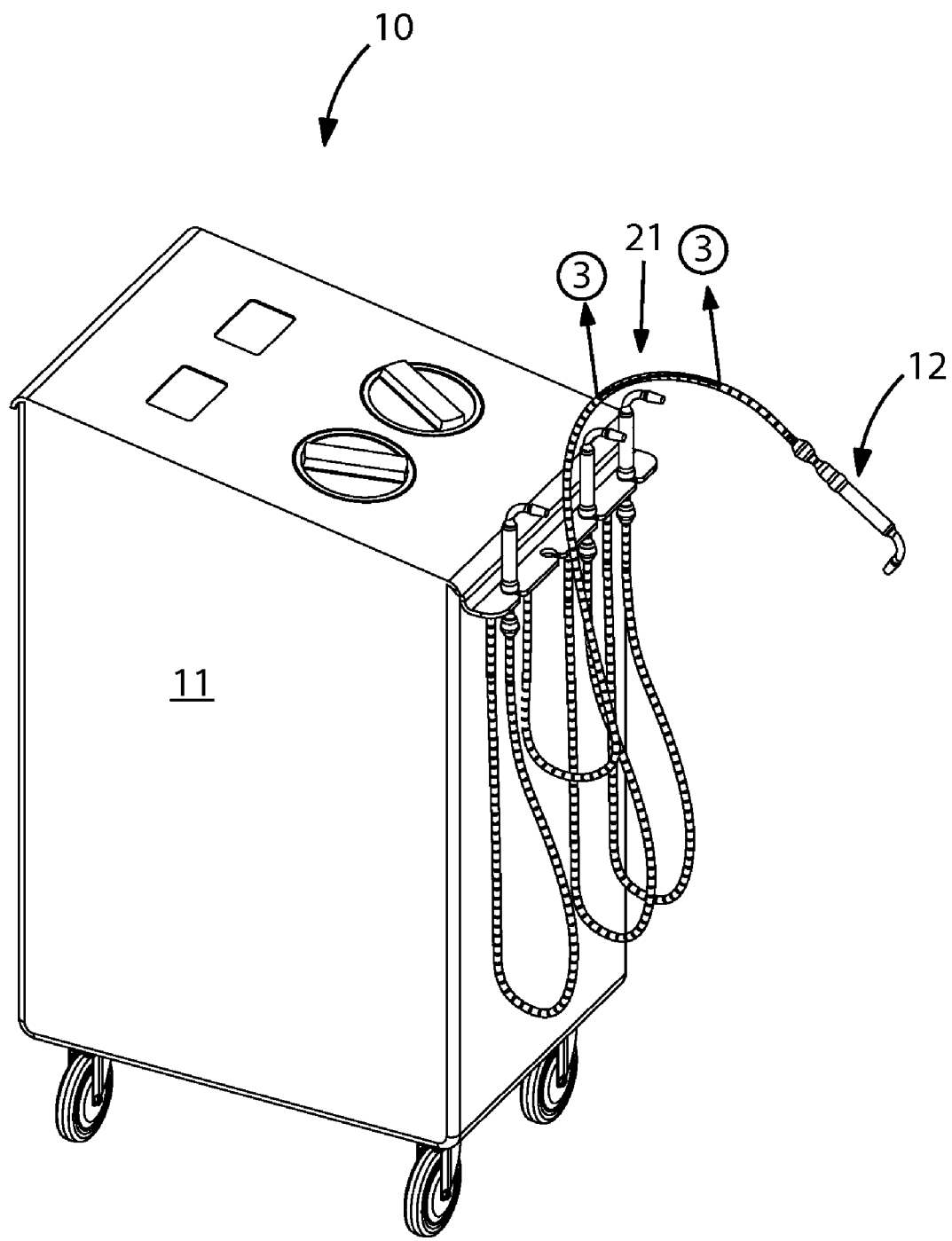
FIG. 2 is a perspective view showing one of the deformably non-resilient appendages retaining a curvilinear tensioned shape while independently supported in the patient oral cavity.

The device of this invention is referred to generally in FIGS. 1-3b and is intended to provide a mobile suction unit 10 for extracting fluid and debris from an oral cavity of a dental patient. It should be understood that the mobile suction unit 10 may be used to effectively hold various dental tools during a dental procedure and should not be limited in use to the applications mentioned herein. Use of the term appendage 21 may define a group of appendages (hoses) as shown in FIGS. 1 and 2. Use of the term dental instrument 12 may define a group of dental instruments 12 as shown in FIGS. 1 and 2.

The deformably non-resilient characteristics of the appendage 21 advantageously provide the unpredictable and unexpected result of preventing a caregiver from tripping over dangling hoses while offering unobstructed visibility of the patient oral cavity during dental procedures. The shape-retaining characteristics of the appendage 21 further enable the dental instrument 12 to remain tautly placed in the patient oral cavity until removed. Thus, a caregiver/patient does not have to hold the appendage 21 or dental instrument 12 while positioned in the patient oral cavity. Such an unexpected and unpredictable advantage allows the caregiver to attend to other duties without having to constantly monitor or handle the appendage 21 or dental instrument 12.

Referring to FIGS. 1-3b in general, the mobile suction unit 10 advantageously alleviates hassles of having a patient hold onto the hose (appendage 21) with his/her hand or mouth, the former of which could result in cramping and the latter of which tends to negatively impinge on mouth tissue. Such a mobile suction unit 10 preferably includes a portable body 11, at least one deformably non-resilient appendage 21 connected to the body 11, and at least one dental instrument 12 connected to the deformably non-resilient appendage 21. It is noted that the body 11 may contain supplies, trash receptacle(s), motorized suction/fluid discharge devices, and other conventional dental equipment, well known in the industry.

Notably, the deformably non-resilient appendage 21 may be selectively bent from a non-tensioned shape (as perhaps best shown in FIGS. 1 and 3a) to a curvilinear tensioned shape (as perhaps best shown in FIGS. 2 and 3b) in such a manner that the deformably non-resilient appendage 21 indefinitely retains the curvilinear tensioned shape while the dental instrument 12 is adapted to be positioned within the patient oral cavity. Such a structural configuration provides the unexpected and unpredictable advantage of enabling the appendage 21 to maintain a fixed deformed shape so that the dental instrument 12 is self-supported in the patient oral cavity (mouth).

In an exemplary embodiment, the dental instruments 12 may preferably extend from body 11 in an upward fashion. Further, the deformably non-resilient appendage 21 may be selectively tensioned to remain stationary within the reach of the caregiver. Of course, the unit 10 may include different types of dental instruments including suction tools, as is obvious to a person of ordinary skill in the art.

In a preferred embodiment, the deformably non-resilient appendage 21 may have a corrugated and non-planar outermost surface 25. Such a deformably non-resilient appendage 21 preferably remains connected to the body 11 and the dental instrument 12 while disposed at the curvilinear tensioned shape.

As perhaps best shown in FIGS. 1-3b, the deformably non-resilient appendage 21 may include an internal conduit 15 having a proximal end in fluid communication with the body 11 and further may have a distal end in fluid communication with the dental instrument 12. It is noted that conduit 15 travels along the entire longitudinal length of appendage 21 so that fluid and debris can be transported between body 11 and the patient oral cavity. Thus, the internal conduit 15 advantageously remains capable of transferring fluid and debris therein while the deformably non-resilient appendage 21 is disposed at the curvilinear tensioned shape. Such a structural configuration provides the unexpected and unpredictable advantage of maintaining the dental instrument 12 at a substantially stable position within the patient oral cavity without requiring the patient/caregiver to hold the appendage 21 or dental instrument 12.

In an exemplary embodiment, the deformably non-resilient appendage 21 may include a first deformable sheath 16 directly engaged about an outer surface of the internal conduit 15. Such a first deformable sheath 16 preferably extends along an entire longitudinal length of the internal conduit 15. It is noted that the first sheath 16 preferably travels along an entire longitudinal length of conduit 15. Notably, the first deformable sheath 16 preferably includes a plurality of first spaced grooves 18 formed therein and concentrically disposed about the internal conduit 15. Such a structural configuration provides the unexpected and unpredictable advantage of enabling the first deformable sheath 16 to freely bend with minimal resistance while retaining the curvilinear tensioned shape.

Figure 3A:
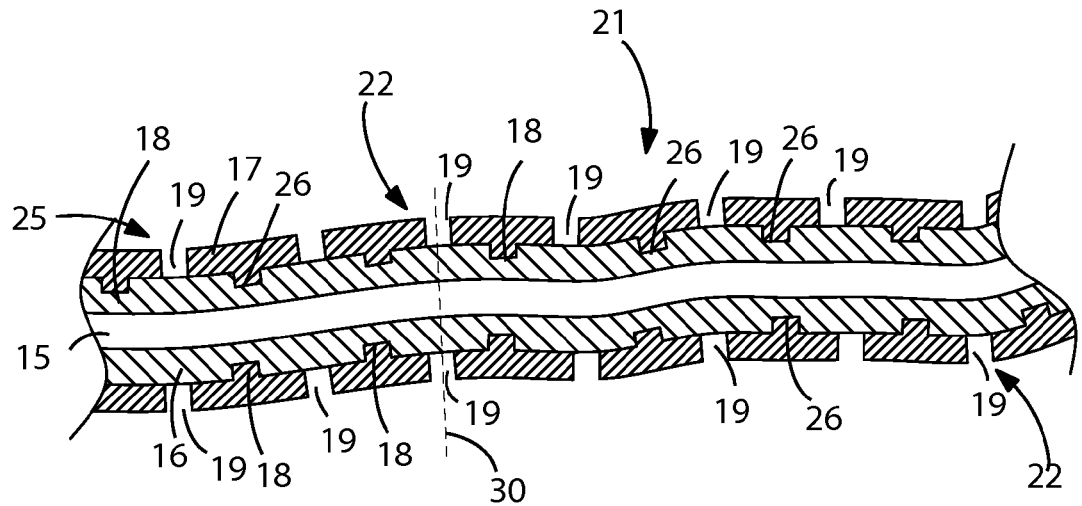
FIG. 3a is an enlarged cross-sectional view showing the relative shape of the internal tube as well as the first and second deformable sheaths while the appendage is at the non-tensioned shape.
Figure 3B:
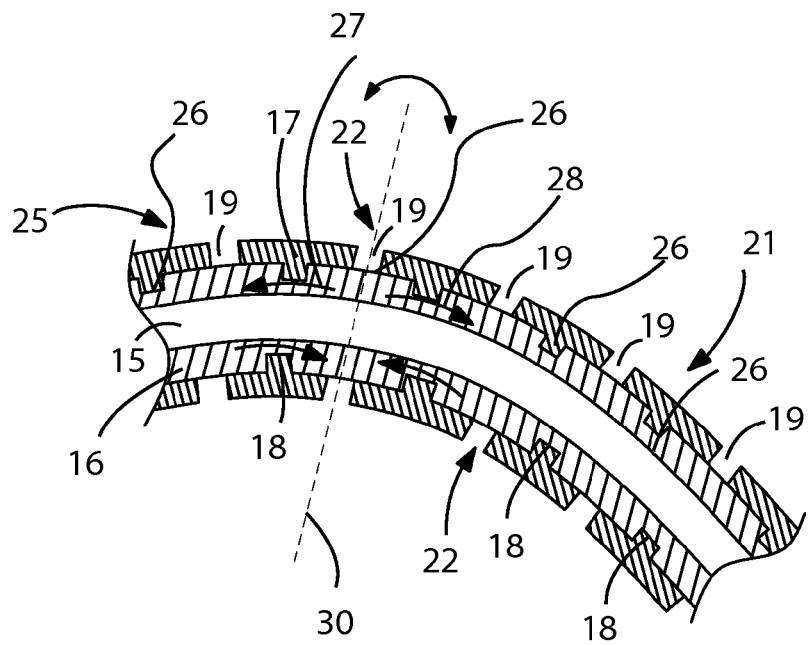
FIG. 3b is enlarged cross-sectional view showing the relative shape of the internal tube as well as the first and second deformable sheaths while the appendage is at the curvilinear tensioned shape.

Still referring to FIGS. 3a-3b, the deformably non-resilient appendage 21 may further include a second deformable sheath 17 directly engaged about an outer surface of the first deformable sheath 16. Such a deformable sheath preferably extends along an entire longitudinal length of the first deformable sheath 16. Notably, the second deformable sheath 17 may include a plurality of second spaced grooves 19 formed therein and concentrically disposed about the internal conduit 15. Such a structural configuration provides the unexpected and unpredictable advantage of enabling the second deformable sheath 17 to freely bend in sync with the first deformable sheath 16 with minimal resistance while retaining the curvilinear tensioned shape.

In an exemplary embodiment, the first and second spaced grooves 19 may be concentrically juxtaposed along a longitudinal length of the internal conduit 15, thereby distributed external tension forces away from fulcrum axis 30 and along the surface area of the appendage 21. Each of the second spaced grooves 19 may have a width 22 defined along the longitudinal length of the appendage 21. In this manner, selected portions of the width 22 are respectively increased and decreased as the second deformable sheath 17 is bent to the curvilinear tensioned shape. Such a structural configuration provides the unexpected and unpredictable advantage of permitting the appendage 21 to retain its curvilinear tensioned shape without resiliently returned back to equilibrium.

As perhaps best shown in FIGS. 3a-3b, the second deformable sheath 17 may further include a plurality tongues 26 statically interfitted within the first spaced grooves 18 respectively. Such tongues 26 preferably exert a shear force 27, 28 directed away from fulcrum axis 30 about which the appendage 21 is bent such that the first deformable sheath 16 is restricted from returning to the non-tensioned shape. Such a structural configuration provides the unexpected and unpredictable advantage of exerting a force along the first deformable sheath 16 that ensures the curvilinear tensioned shape is maintained.

In an exemplary embodiment, the first deformable sheath 16 preferably remains intercalated between the second deformable sheath 17 and the outer surface of the internal conduit 15. Such a structural configuration provides the unexpected and unpredictable advantage of transmitting forces 27, 28 between the conduit 15 and second deformable sheath 17.

Referring back to FIGS. 1-2, in an exemplary embodiment, a holster 23 may be located along a top edge of the body 11 wherein the dental instruments 12 may be removably nested at the holster 23 during non-use. Additionally, the mobile unit 10 may also include wheels 24 for easy transport. In an alternative embodiment, the device may be incorporated into conventional suction units.

The present disclosure may further include a method of utilizing a mobile suction unit 10 for extracting fluid and debris from an oral cavity of a patient, the method including the chronological steps of: providing a portable body 11; providing and connecting a deformably non-resilient appendage 21 to the body 11 wherein the deformably non-resilient appendage 21 may have a corrugated and non-planar outermost surface 25; and providing and connecting a dental instrument 12 to the deformably non-resilient appendage 21.

Such a method may further include the chronological steps of: selectively bending the deformably non-resilient appendage 21 from a non-tensioned shape to a curvilinear tensioned shape; positioning the dental instrument 12 within the patient oral cavity; and the deformably non-resilient appendage 21 indefinitely retaining the curvilinear tensioned shape while the dental instrument 12 is positioned within the patient oral cavity.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention. In particular, with respect to the above description, it is to be realized that the optimum dimensional relationships for the parts of the present invention may include variations in size, materials, shape, form, function and manner of operation.

What is claimed as new and what is desired to secure by Letters Patent of the United States is:

1. A mobile suction unit for extracting fluid and debris from an oral cavity of a patient, said mobile suction unit comprising:
    a portable body;
    a deformably non-resilient appendage connected to said body; and
    a dental instrument connected to said deformably non-resilient appendage;
    wherein said deformably non-resilient appendage is selectively bent from a non-tensioned shape to a curvilinear tensioned shape in such a manner that said deformably non-resilient appendage indefinitely retains said curvilinear tensioned shape while said dental instrument is adapted to be positioned within the patient oral cavity;
    wherein said deformably non-resilient appendage comprises: an internal conduit having a proximal end in fluid communication with said body and further having a distal end in fluid communication with said dental instrument, said internal conduit remaining capable of transferring fluid and debris therein while said deformably non-resilient appendage is disposed at said curvilinear tensioned shape;
    wherein said deformably non-resilient appendage comprises: a first deformable sheath directly engaged about an outer surface of said internal conduit, said first deformable sheath extending along an entire longitudinal length of said internal conduit;
    wherein said first deformable sheath includes a plurality of first spaced grooves formed therein and concentrically disposed about said internal conduit;
    wherein said deformably non-resilient appendage further comprises: a second deformable sheath directly engaged about an outer surface of said first deformable sheath, said second deformable sheath extending along an entire longitudinal length of said first deformable sheath;
    wherein said second deformable sheath includes a plurality of second spaced grooves formed therein and concentrically disposed about said internal conduit;
    wherein said first and second spaced grooves are concentrically juxtaposed along a longitudinal length of said internal conduit, each of said second spaced grooves having a width defined along the longitudinal length of said deformably non-resilient appendage;
    wherein selected portions of said width are respectively increased and decreased as said second sheath is bent to said curvilinear tensioned shape;
    wherein said second deformable sheath further comprises: a plurality of tongues statically interfitted within said first spaced grooves respectively, wherein said tongues exert a shear force directed away from a fulcrum axis about which said appendage is bent such that said first deformable sheath is restricted from returning to said non-tensioned shape;
    wherein said first deformable sheath remains intercalated between said second deformable sheath and said outer surface of said internal conduit;
    wherein said second sheath is prohibited from disengaging said first sheath and maintains continuous direct contact with said first sheath.

2. The mobile suction unit of claim 1, wherein said deformably non-resilient appendage remains connected to said body and said dental instrument while disposed at said curvilinear tensioned shape.

3. The mobile suction unit of claim 1, further comprising: a holster located along a top edge of said body, said dental instruments being removably nested at said holster during non-use.

4. A mobile suction unit for extracting fluid and debris from an oral cavity of a patient, said mobile suction unit comprising:
    a portable body;
    a deformably non-resilient appendage connected to said body; and
    a dental instrument connected to said deformably non-resilient appendage;
    wherein said deformably non-resilient appendage is selectively bent from a non-tensioned shape to a curvilinear tensioned shape in such a manner that said deformably non-resilient appendage indefinitely retains said curvilinear tensioned shape while said dental instrument is adapted to be positioned within the patient oral cavity;
    wherein said deformably non-resilient appendage has a corrugated and non-planar outermost surface;
    wherein said deformably non-resilient appendage comprises: an internal conduit having a proximal end in fluid communication with said body and further having a distal end in fluid communication with said dental instrument, said internal conduit remaining capable of transferring fluid and debris therein while said deformably non-resilient appendage is disposed at said curvilinear tensioned shape;
    wherein said deformably non-resilient appendage comprises: a first deformable sheath directly engaged about an outer surface of said internal conduit, said first deformable sheath extending along an entire longitudinal length of said internal conduit;
    wherein said first deformable sheath includes a plurality of first spaced grooves formed therein and concentrically disposed about said internal conduit;
    wherein said deformably non-resilient appendage further comprises: a second deformable sheath directly engaged about an outer surface of said first deformable sheath, said second deformable sheath extending along an entire longitudinal length of said first deformable sheath;
    wherein said second deformable sheath includes a plurality of second spaced grooves formed therein and concentrically disposed about said internal conduit;

wherein said second sheath is prohibited from disengaging said first sheath and maintains continuous direct contact with said first sheath.

5. The mobile suction unit of claim 4, wherein said deformably non-resilient appendage remains connected to said body and said dental instrument while disposed at said curvilinear tensioned shape.

6. The mobile suction unit of claim 4, wherein said first and second spaced grooves are concentrically juxtaposed along a longitudinal length of said internal conduit, each of said second spaced grooves having a width defined along the longitudinal length of said deformably non-resilient appendage;

wherein selected portions of said width are respectively increased and decreased as said second sheath is bent to said curvilinear tensioned shape.

7. The mobile suction unit of claim 4, wherein said second deformable sheath further comprises: a plurality of tongues statically interfitted within said first spaced grooves respectively, wherein said tongues exert a shear force directed away from a fulcrum axis about which said appendage is bent such that said first deformable sheath is restricted from returning to said non-tensioned shape.

8. The mobile suction unit of claim 4, wherein said first deformable sheath remains intercalated between said second deformable sheath and said outer surface of said internal conduit.

9. The mobile suction unit of claim 4, further comprising: a holster located along a top edge of said body, said dental instruments being removably nested at said holster during non-use.

\* \* \* \* \*